United States Patent
Eversole et al.

(10) Patent No.: US 10,564,081 B2
(45) Date of Patent: Feb. 18, 2020

(54) SYSTEM AND METHOD FOR EVALUATING EDGE HARDNESS OF CEMENTITIOUS BOARDS AND SYSTEM FOR STACKING CEMENTITIOUS BOARDS INLCUDING SAME

(71) Applicant: United States Gypsum Company, Chicago, IL (US)

(72) Inventors: Leslie Eversole, Milton, PA (US);
Colin J. Fahey, Elysburg, PA (US);
Thomas Boyer, Bloomsburg, PA (US);
Craig Thomas Watson, McEwensville, PA (US)

(73) Assignee: UNITED STATES GYPSUM COMPANY, Chicago, IL (US)

( * ) Notice: Subject to any disclaimer, the term of this patent is extended or adjusted under 35 U.S.C. 154(b) by 228 days.

(21) Appl. No.: 15/729,398

(22) Filed: Oct. 10, 2017

(65) Prior Publication Data
US 2018/0224364 A1   Aug. 9, 2018

Related U.S. Application Data

(60) Provisional application No. 62/454,664, filed on Feb. 3, 2017.

(51) Int. Cl.
*G01N 3/42* (2006.01)
*B65G 57/10* (2006.01)
(Continued)

(52) U.S. Cl.
CPC ............... *G01N 3/42* (2013.01); *B65G 57/10* (2013.01); *B65G 57/112* (2013.01); *B65G 57/18* (2013.01)

(58) Field of Classification Search
CPC .. G01N 3/40; G01N 3/46; G01N 3/42; G01N 2203/0098; G01N 3/48; G01N 2203/0248;
(Continued)

(56) References Cited

U.S. PATENT DOCUMENTS 3,017,305 A   8/1956   Dailey
2,985,219 A   5/1961   Summerfield
(Continued)

FOREIGN PATENT DOCUMENTS

CN   106353210 A   1/2017
EP   1132710 A1   9/2001
(Continued)

OTHER PUBLICATIONS

Standard Test Methods for Physical Testing of Gypsum Panel Products, Nov. 2016, ASTM international (Year: 2016).*
(Continued)

*Primary Examiner* — John Fitzgerald
*Assistant Examiner* — Truong D Phan
(74) *Attorney, Agent, or Firm* — Leydig, Voit & Mayer, Ltd.; Philip T. Petti; Pradip K. Sahu

(57) ABSTRACT

Embodiments of a system and a method for determining an edge hardness value for a cementitious board can be used to effectively determine the hardness of the board after it has been made and dried at a predetermined location, such as, at a stacking station, for example. An actuator assembly can manipulate a punch such that the punch is inserted into one of the edges of one of the cementitious boards in the stacker in a controlled manner. A force gauge can be associated with the punch to measure the resistance force exerted by the cementitious board in response to the punch being inserted into its edge. The measured resistance force can be used to determine the edge hardness value.

20 Claims, 4 Drawing Sheets

(51) Int. Cl.
  *B65G 57/11*    (2006.01)
  *B65G 57/18*    (2006.01)
  *B65G 57/112*   (2006.01)

(58) Field of Classification Search
  CPC ... G01N 2203/0282; G01N 2203/0676; G01N 33/383; B28B 17/0072; B28B 19/0015; B28B 19/0092; B65G 57/10; B65G 57/112; B65G 57/18
  USPC .................................................. 73/78, 81, 82
  See application file for complete search history.

(56) References Cited

U.S. PATENT DOCUMENTS

| | | | |
|---|---|---|---|
| 3,359,146 | A | 12/1967 | Lane |
| 3,832,250 | A | 8/1974 | Pearson |
| 4,279,673 | A | 7/1981 | White et al. |
| 4,852,397 | A | 8/1989 | Haggag |
| 5,146,779 | A | 9/1992 | Sugimoto et al. |
| 5,320,677 | A | 6/1994 | Baig |
| 5,342,566 | A | 8/1994 | Schäfer et al. |
| 5,643,510 | A | 7/1997 | Sucech |
| 5,673,708 | A * | 10/1997 | Athanasiou ............ A61B 5/103 600/587 |
| 5,683,635 | A | 11/1997 | Sucech et al. |
| 5,817,301 | A * | 10/1998 | Lamplough .......... A61K 8/0229 424/70.1 |
| 6,247,356 | B1 | 6/2001 | Merck, Jr. et al. |
| 6,279,388 | B1 | 8/2001 | Tsujii et al. |
| 6,494,609 | B1 | 12/2002 | Wittbold et al. |
| 6,508,110 | B1 * | 1/2003 | Lin ........................ B82Y 35/00 73/105 |
| 6,615,565 | B2 | 9/2003 | Dekker |
| 6,691,564 | B2 | 2/2004 | Anderberg |
| 6,874,930 | B2 | 4/2005 | Wittbold et al. |
| 7,007,914 | B2 | 3/2006 | Petersen et al. |
| 7,223,311 | B2 | 5/2007 | Conboy |
| 7,296,919 | B2 | 11/2007 | Petersen et al. |
| 7,681,438 | B2 | 3/2010 | Albadri et al. |
| 8,234,912 | B2 | 8/2012 | Suarez-Rivera et al. |
| 8,281,648 | B2 | 10/2012 | Leroux |
| 8,323,785 | B2 | 12/2012 | Yu et al. |
| 2001/0001218 | A1 | 5/2001 | Luongo |
| 2002/0044857 | A1 | 4/2002 | Dekker |
| 2003/0147737 | A1 | 8/2003 | Pfeiffer et al. |
| 2006/0045975 | A1 | 3/2006 | Yamaji et al. |
| 2006/0144497 | A1 | 7/2006 | Capron |
| 2007/0023118 | A1 | 2/2007 | Spielvogel |
| 2010/0119776 | A1 | 5/2010 | Frank |
| 2011/0055982 | A1 * | 3/2011 | Watanabe ............... G01Q 10/02 850/2 |
| 2011/0112397 | A1 * | 5/2011 | Shen ...................... A61B 34/20 600/424 |
| 2012/0085154 | A1 * | 4/2012 | Takemura ................ G01N 3/42 73/81 |
| 2012/0168527 | A1 | 7/2012 | Li et al. |
| 2012/0170403 | A1 | 7/2012 | Li et al. |
| 2012/0295059 | A1 | 11/2012 | Frank |
| 2012/0322904 | A1 * | 12/2012 | Fisher ................... C04B 28/146 521/139 |
| 2013/0098268 | A1 | 4/2013 | Li et al. |
| 2013/0099027 | A1 | 4/2013 | Li et al. |
| 2013/0099418 | A1 | 4/2013 | Li et al. |
| 2013/0100759 | A1 | 4/2013 | Wittbold et al. |
| 2013/0216717 | A1 | 8/2013 | Rago et al. |
| 2013/0233880 | A1 | 9/2013 | Rego et al. |
| 2013/0308411 | A1 | 11/2013 | Wittbold et al. |
| 2014/0158273 | A1 | 6/2014 | Yu et al. |
| 2015/0094839 | A1 | 4/2015 | DellAngelo et al. |
| 2015/0285722 | A1 | 10/2015 | Wu et al. |

FOREIGN PATENT DOCUMENTS

| | | |
|---|---|---|
| EP | 2104855 B1 | 10/2012 |
| JP | 2014-098961 A | 5/2014 |

OTHER PUBLICATIONS

English Translation, Sakuma, Multi-dimensional drive control apparatus, multi-dimensional drive control program, and indentation testing system, May 2014 (Year: 2014).*

ASTM Designation C-473-07, "Standard Test Methods for Physical Testing of Gypsum Panel Products," 287-300 (2009).

European Patent Office, International Search Report and the Written Opinion in International Application No. PCT/US2018/016553 (dated May 14, 2018).

Bent Tram A/S Mechanical Testing Solutions, "ASTM C473—Standard Test Methods for Physical Testing of Gypsum Panel Products" 2 pages (Accessed Jun. 17, 2016).

Georgia Pacific, "Evaluation of the 1/2" DensGlass Gold Sheathing to ASTM C1177/C1177 M-06, *Progressive Engineering Inc.*, 21 pages (Feb. 8, 2010).

* cited by examiner

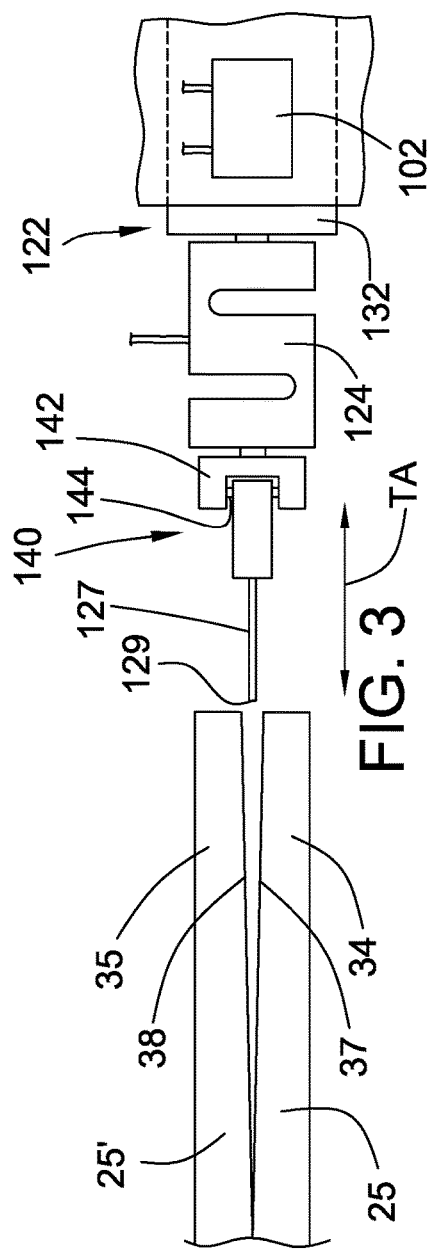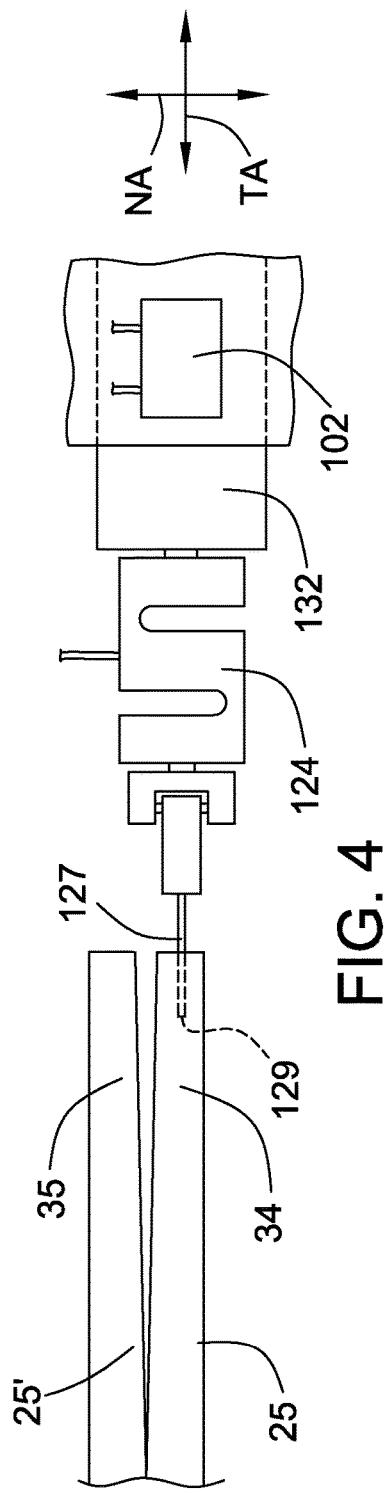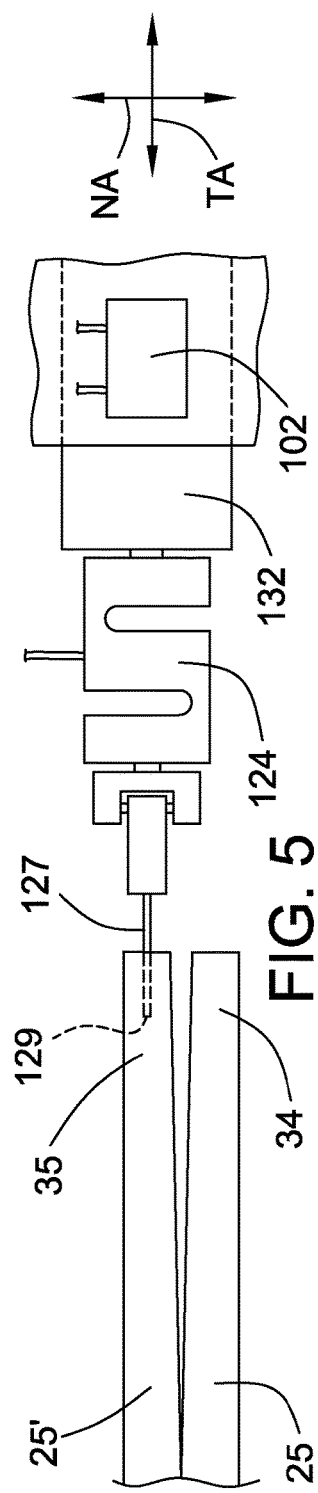

SYSTEM AND METHOD FOR EVALUATING EDGE HARDNESS OF CEMENTITIOUS BOARDS AND SYSTEM FOR STACKING CEMENTITIOUS BOARDS INLCUDING SAME

CROSS-REFERENCE TO RELATED APPLICATION

This patent application claims the benefit of priority to U.S. Provisional Patent Application No. 62/454,664, filed Feb. 3, 2017, and entitled "System And Method For Evaluating Edge Hardness Of Cementitious Boards And System For Stacking Cementitious Boards Including Same," which is incorporated by reference in its entirety herein.

BACKGROUND

The present disclosure relates to cementitious board manufacturing processes and, more particularly, to systems and methods for measuring the hardness of the edge of a cementitious board after its manufacture.

In many types of cementitious articles, set gypsum (calcium sulfate dihydrate) is often a major constituent. For example, set gypsum is a major component of end products created by use of traditional plasters (e.g., plaster-surfaced internal building walls), and also in faced gypsum board employed in typical drywall construction of interior walls and ceilings of buildings. In addition, set gypsum is the major component of gypsum/cellulose fiber composite boards and products, as described in U.S. Pat. No. 5,320,677, for example. Typically, such gypsum-containing cementitious products are made by preparing a mixture of calcined gypsum (calcium sulfate alpha or beta hemihydrate and/or calcium sulfate anhydrite), water, and other components, as appropriate to form cementitious slurry. The cementitious slurry and desired additives are often blended in a continuous mixer, as described in U.S. Pat. No. 3,359,146, for example.

In a typical cementitious board manufacturing process such as gypsum wallboard, cementitious board is produced by uniformly dispersing calcined gypsum (commonly referred to as "stucco") in water to form aqueous calcined gypsum slurry. The aqueous calcined gypsum slurry is typically produced in a continuous manner by inserting stucco and water and other additives into a mixer which contains means for agitating the contents to form a uniform gypsum slurry. The slurry is continuously directed toward and through a discharge outlet of the mixer and into a discharge conduit connected to the discharge outlet of the mixer. Aqueous foam can be combined with the aqueous calcined gypsum slurry in the mixer and/or in the discharge conduit. A stream of foamed slurry passes through the discharge conduit from which it is continuously deposited onto a moving web of cover sheet material (i.e., the face sheet) supported by a forming table. The foamed slurry is allowed to spread over the advancing face sheet. A second web of cover sheet material (i.e., the back sheet) is applied to cover the foamed slurry and form a sandwich structure of a continuous wallboard preform. The wallboard preform is subjected to forming, such as at a conventional forming station, to obtain a desired thickness.

The calcined gypsum reacts with the water in the wallboard preform to form a matrix of crystalline hydrated gypsum or calcium sulfate dihydrate and sets as a conveyor moves the wallboard preform down the manufacturing line. The hydration of the calcined gypsum provides for the formation of an interlocking matrix of set gypsum, thereby imparting strength to the gypsum structure in the gypsum-containing product. The product slurry becomes firm as the crystal matrix forms and holds the desired shape.

After the wallboard preform is cut into segments downstream of the forming station at a point along the line where the preform has set sufficiently, the segments are flipped over, dried (e.g., in a kiln) to drive off excess water, and processed to provide the final wallboard product of desired dimensions. The aqueous foam produces air voids in the set gypsum, thereby reducing the density of the finished product relative to a product made using a similar slurry but without foam. Dried boards are typically sold in pairs in which the two boards are arranged with their face sheets arranged inwardly (a process called "booking") to help protect the face sheets from becoming marred during transportation and handling. Booked pairs of boards can be stacked on top of each other at a stacking unit to facilitate bundling and palletization. Prior devices and methods for addressing some of the operational problems associated with the production of gypsum wallboard are disclosed in commonly-assigned U.S. Pat. Nos. 5,683,635; 5,643,510; 6,494,609; 6,874,930; 7,007,914; and 7,296,919, which are incorporated by reference.

Gypsum wallboard is typically installed by securing the board to a framing structure using a plurality of fasteners. The installer follows a fastener schedule in which a number of fasteners are used along the long edges of the board. Typically, more fasteners are required along the edges of the board than are used in the field of the board. Furthermore, during transport of gypsum wallboard, the edges of the board are typically grasped by the installer to manipulate the board.

With the core of the board being made from increasingly less dense gypsum slurry, it can be desirable to position a more dense and/or stronger slurry at the edges of the board to help allow for the handling of the board without excessive damage to its edges and also to allow for the secure attachment of the board to a framing structure via fasteners located at the edges of the board. U.S. Pat. Nos. 2,985,219 and 4,279,673 describe various methods for producing foamed gypsum board having edges that are denser and harder than the core portion of the board, such as, by diverting a portion of the foamed slurry from the main slurry mixing chamber. The diverted portion is then treated separately in one or more supplementary mixers with high agitation and/or defoaming agents to remove all or most of the foam and thus produce a harder, denser "edge" slurry to be cast at the edges of the cover sheet so that it comes into contact with the sides of the cast main slurry stream.

Should the board edges be too hard, other problems can occur. For example, edges that are too hard can produce fastener failures manifested as fasteners being pulled out of the framing structure. Also, when board with edges that are too hard is dropped, it can break at a lateral position along its width that is too far inward and/or to a greater degree, than one would find acceptable.

Gypsum wallboard manufacturers typically evaluate the hardness of the edges of the board to determine the board's ability to resist being crushed during handling or installation. For example, ASTM International's ASTM Standard C473-16, which is entitled, "Standard Test Methods for Physical Testing of Gypsum Panel Products," sets forth a test procedure for measuring board edge hardness using a steel punch. During the manufacture of the gypsum boards, an operator may periodically test the edge hardness of the dried board to verify that a certain degree of edge hardness is being obtained. For example, an operator can use a handheld hardness tester to assess the hardness of the board edges as the boards come to rest near a stacking machine.

There is a continued need in the art to provide additional solutions to enhance the production of cementitious boards. For example, there is a continued need for techniques for measuring the edge hardness of cementitious boards that have enhanced efficiency and repeatability.

It will be appreciated that this background description has been created by the inventor to aid the reader and is not to be taken as an indication that any of the indicated problems were themselves appreciated in the art. While the described principles can, in some aspects and embodiments, alleviate the problems inherent in other systems, it will be appreciated that the scope of the protected innovation is defined by the attached claims and not by the ability of any disclosed feature to solve any specific problem noted herein.

SUMMARY

In one aspect, the present disclosure is directed to embodiments of a system for determining an edge hardness value of a cementitious board. For example, in one embodiment, a system for determining an edge hardness value of a cementitious board is disclosed in which the cementitious board has a cementitious core formed from an aqueous cementitious slurry, first and second faces with a length extending along a longitudinal axis and a width extending along a transverse axis that is perpendicular to the longitudinal axis, and first and second edges with a thickness extending along a normal axis that is perpendicular to both the longitudinal axis and the transverse axis. The system includes a support fixture, a punch, an actuator assembly, a force gauge, and a processor.

The support fixture has a support surface configured to support the cementitious board such that the first and second faces are generally parallel to the support surface. The punch has a cylindrical distal portion with a distal end.

The actuator assembly includes a first actuator and a second actuator. The second actuator supports the punch. The first actuator is configured to move the punch along the normal axis relative to the cementitious board supported in the support fixture to adjust the position of the punch relative to the thickness of the cementitious board. The second actuator is configured to move the punch along the transverse axis relative to the cementitious board supported in the support fixture to adjust the position of the punch relative to the width of the cementitious board. The second actuator is configured to reciprocally move the punch along the transverse axis over a measurement stroke between a home position, in which the distal end of the punch is in offset relationship to the cementitious board supported in the support fixture, and a measurement position, in which the distal end of the punch is in interfering relationship with the cementitious board supported in the support fixture, such that the second actuator is configured to drive the distal end of the punch into one of the first and second edges of the cementitious board supported in the support fixture when the punch moves from the home position to the measurement position.

The force gauge is supported by the second actuator of the actuator assembly and is interposed between the punch and the second actuator. The force gauge is configured to measure a resistance force exerted against the punch by the cementitious board in response to the distal end of the punch being inserted into the edge of the cementitious board. The force gauge is configured to generate a force signal indicative of the resistance force.

The processor is in communication with the force gauge to receive the force signal therefrom. The processor is programmed with an edge hardness measurement program stored on a non-transitory computer readable medium. The edge hardness measurement program is configured to use the force signal to determine the edge hardness value for the cementitious board.

In another aspect of the present disclosure, embodiments of a stacking system for stacking a plurality of cementitious boards are described. For example, in one embodiment, a stacking system for stacking a plurality of cementitious boards is disclosed in which each cementitious board has a cementitious core formed from an aqueous cementitious slurry, first and second faces with a length extending along a longitudinal axis and a width extending along a transverse axis that is perpendicular to the longitudinal axis, and first and second edges with a thickness extending along a normal axis that is perpendicular to both the longitudinal axis and the transverse axis. The stacking system includes a lift assembly, a conveyor, a punch, an actuator assembly, a force gauge, and a processor.

The lift assembly is configured to support the cementitious boards in a stacked arrangement upon the support surface. The lift assembly includes a support fixture and a hoist. The support fixture has a support surface configured to support the cementitious boards such that the first and second faces of the cementitious boards are generally parallel to the support surface. The hoist is connected to the support fixture and is adapted to move the support fixture over a range of travel along the normal axis. The conveyor is configured to serially convey the cementitious boards to a position over the lift assembly for being placed upon the support surface.

The punch has a cylindrical distal portion with a distal end. The actuator assembly is configured to reciprocally move the punch along the transverse axis relative to the support fixture over a measurement stroke between a home position, in which the distal end of the punch is in offset relationship to the cementitious boards supported in the support fixture, and a measurement position, in which the distal end of the punch is in interfering relationship with one of the cementitious boards supported in the support fixture, such that the actuator assembly drives the distal end of the punch into one of the first and second edges of said cementitious board when the punch moves from the home position to the measurement position.

The force gauge is supported by the actuator assembly and is interposed between the punch and the actuator assembly. The force gauge is configured to measure a resistance force exerted against the punch by said cementitious board in response to the distal end of the punch being inserted into the edge of said cementitious board. The force gauge is configured to generate a force signal indicative of the resistance force.

The processor is in communication with the force gauge to receive the force signal therefrom. The processor is programmed with an edge hardness measurement program stored on a non-transitory computer readable medium. The edge hardness measurement program is configured to use the force signal to determine the edge hardness value for the cementitious board.

In yet another aspect of the present disclosure, embodiments of a method of determining an edge hardness value of a cementitious board are described. For example, in one embodiment, a method of determining an edge hardness value of a cementitious board can be used with a cementitious board that has a cementitious core formed from aqueous cementitious slurry, first and second faces with a length extending along a longitudinal axis and a width extending along a transverse axis that is perpendicular to the longitudinal axis, and first and second edges with a thickness extending along a normal axis that is perpendicular to both the longitudinal axis and the transverse axis.

The method includes conveying the cementitious board to a position over a support surface of a lift assembly such that the support surface supports the cementitious board with the first and second faces being generally parallel to the support surface. A punch is positioned along the normal axis relative to the cementitious board supported by the support surface such that the punch is positioned along the normal axis within the thickness of the cementitious board. The punch is moved along the transverse axis relative to the cementitious board supported by the support surface over a measurement stroke between a home position, in which a distal end of the punch is in offset relationship to the cementitious board, and a measurement position, in which the distal end of the punch is in interfering relationship with the cementitious board, such that the distal end of the punch is inserted into one of the first and second edges of said cementitious board when the punch is in the measurement position.

A resistance force, which is exerted by the cementitious board against the punch in response to the punch being inserted into one of the first and second edges of said cementitious board, is measured. A force signal is transmitted to a processor. The force signal is indicative of the measured resistance force. An edge hardness measurement program stored upon a non-transitory computer-readable medium is executed using the processor to determine the edge hardness value for the cementitious board based upon the force signal.

Further and alternative aspects and features of the disclosed principles will be appreciated from the following detailed description and the accompanying drawings. As will be appreciated, the systems and techniques for measuring the degree to which cementitious slurry has set during the manufacture of a cementitious article that are disclosed herein are capable of being carried out and used in other and different embodiments, and capable of being modified in various respects. Accordingly, it is to be understood that both the foregoing general description and the following detailed description are exemplary and explanatory only and do not restrict the scope of the appended claims.

BRIEF DESCRIPTION OF THE DRAWINGS

FIG. 3 is a fragmentary, schematic, and further enlarged detail view of the system for determining cementitious board edge hardness of FIG. 2, illustrating a punch in a home position and centered between a pair of booked cementitious boards.

FIG. 4 is a view as in FIG. 3 of the system for determining cementitious board edge hardness of FIG. 2, illustrating the punch in a measurement position in a first cementitious board of the pair of booked cementitious boards.

FIG. 5 is a view as in FIG. 3 of the system for determining cementitious board edge hardness of FIG. 2, illustrating the punch in the measurement position in a second cementitious board of the pair of booked cementitious boards.

Figure 1:
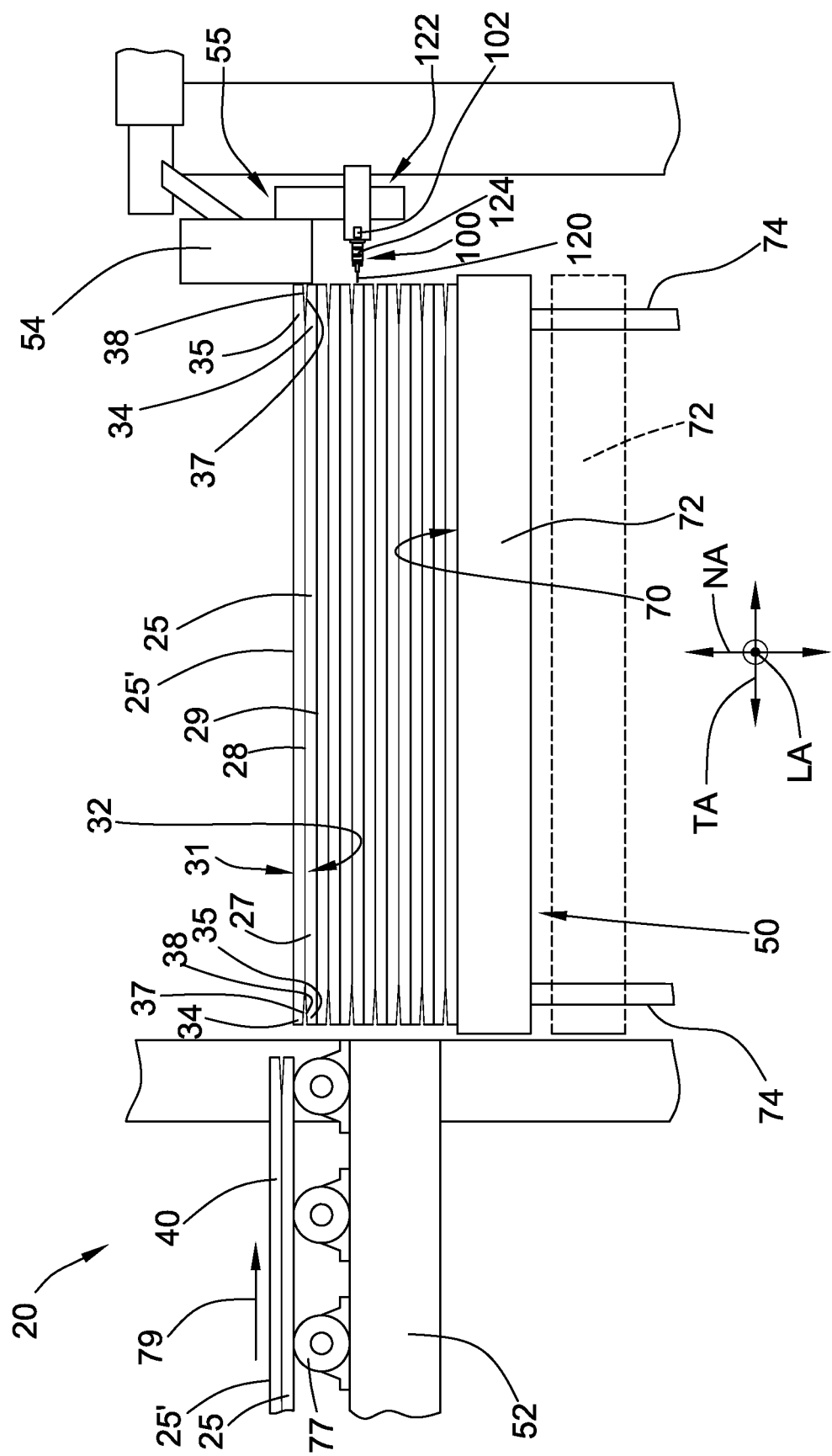
FIG. 1 is a fragmentary, schematic side elevational view of an embodiment of a system for stacking cementitious boards which is constructed in accordance with principles of the present disclosure and which is positioned at a location along a cementitious board manufacturing line at which the cementitious boards are dried, the system including an embodiment of a system for determining an edge hardness value of a cementitious board which is constructed in accordance with principles of the present disclosure.

It should be understood that the drawings are not necessarily to scale and that the disclosed embodiments are sometimes illustrated diagrammatically and in partial views. In certain instances, details which are not necessary for an understanding of this disclosure or which render other details difficult to perceive may have been omitted. It should be understood that this disclosure is not limited to the particular embodiments illustrated herein.

DETAILED DESCRIPTION OF EXEMPLARY EMBODIMENTS

The present disclosure provides various embodiments of a system and a method for measuring an edge hardness of cementitious board having means and steps for determining an edge hardness value of cementitious boards that can be used in connection with the manufacture of various cementitious products, including gypsum wallboard, for example. Embodiments following principles of the present disclosure of a system and a method for determining board edge hardness can be used in a manufacturing environment at a predetermined location to effectively determine the hardness of the set and dried cementitious core (made from an aqueous cementitious slurry) that forms the edge of the cementitious board. In embodiments following principles of the present disclosure, a system for measuring the edge hardness of a cementitious board can be configured as an automatic system for determining edge hardness at a point in the production process after it is dried (e.g., in a kiln), such as, at or near a stacking station, for example.

In embodiments, a system for measuring cementitious board edge hardness includes a cylindrical punch, a force gauge, and an actuator assembly. The punch, which in embodiments can be in the form of a steel punch and constructed according to ASTM Standard C473-16, can be associated with the force gauge, which in embodiments can be a compression-type load cell or other suitable force measuring device or gauge. The actuator assembly (e.g., an X-Y linear actuator) can support the force gauge and the punch and can be configured to selectively move the force gauge-and-punch assembly over a reciprocal range of travel between a home position and a measurement position to contact the cementitious board being supported by the stacker's lift assembly, for example, such that the punch is driven from the home position over a predetermined distance (e.g., ⅝ in.) into the edge of the cementitious board to the measurement position.

The force gauge can be configured to measure the resistance force exerted by the cementitious board against the punch in response to the punch being driven by the actuator assembly into the edge of the cementitious board. The measurement of the edge hardness characteristic of the cementitious board can be based on the measurement of the resistance force generated in response to inserting the punch into the cementitious board is a measure of its hardness. The resistance force is correlated to the compressive strength of the cementitious board and the edge hardness of the cementitious board.

In embodiments, the resistance force data are transmitted to a processor. An edge hardness measurement program stored upon a non-transitory computer-readable medium can be executed using the processor to determine a numerical value relating to the edge hardness of the cementitious board based upon the resistance force generated by the cementitious board in response to the punch being inserted into one of its edges. In embodiments, the edge hardness measurement program is configured to determine an edge hardness value (expressed for example in pounds-force or Newtons) of the edge of the cementitious board based upon a peak load of the resistance force measured for the particular edge of the cementitious board.

Embodiments of a system for determining the edge hardness of cementitious boards following principles of the present disclosure can include a board detection system configured to detect a number of board parameters. The board detection system can include a laser distance sensor mounted in a location where the laser distance sensor can be used on a cementitious board that is placed in a stack of cementitious board upon a support surface of a lift assembly in the stacking area of the dry end of the manufacturing line. The board detection system can be configured to detect the location of the edges of the board, to determine the thickness of the board being tested, and to determine which edge of the board is adjacent the edge hardness punch.

In embodiments, the X-Y actuator assembly can be controlled via an electronic control unit using the information from the board detection system to move the edge hardness punch to the appropriate vertical position and to extend the needle laterally into the board by a predetermined amount (e.g., a ½ inch). The force gauge is configured to detect the amount of force necessary to drive the needle the predetermined distance into the edge of the board. The edge hardness measurement system can repeat the test for the "other" edge of an adjacent board that is booked together with the first board. After each test, the edge hardness measurement system retracts the edge hardness punch and returns it to a home position so that it is clear of the board stack. The edge hardness measurement system can include a processor that is configured to receive time data, side data, and resistance force data for each edge hardness measurement taken by the system and to store this edge hardness measurement data in real time in a database.

Embodiments of a system for measuring the edge hardness of a cementitious board following principles of the present disclosure can be used to carry out a method of determining edge hardness of a cementitious board to automatically measure edge hardness without the need to use a human operator to manually perform a punch test, thereby helping to reduce operator intervention, labor, and variability. For example, use of the measured resistance force by the processor, which is specially programmed with an edge hardness measurement program, can be used rather than relying upon manual testing in determining the edge hardness of the cementitious board. The resistance force measured using an embodiment of a system constructed according to principles of the present disclosure is developed using a controller that moves the punch over a measurement stroke that is substantially consistent over multiple edge hardness measurements in a repeatable fashion and can be used by the processor to determine edge hardness data for the cementitious board in an online manner as it is in being manufactured under conditions which allow for reliable comparison of data over different time periods and different operator shifts.

Embodiments of a system for determining the edge hardness of cementitious boards following principles of the present disclosure can be useful to automatically measure the hardness of the edge of the cementitious board after it is dried. In embodiments, the measurement of edge hardness can be performed automatically and be fed as an input to a process control computer to identify when the cementitious board exhibits an edge hardness that is out of a predetermined edge hardness range (e.g., either too soft or too hard). In embodiments, the system can be configured to issue an operator alert when the edge hardness value determined by the system falls outside of a target edge hardness range (either too soft or too hard). The system can be used to directly determine cementitious board edge hardness and transmit the measured value electronically to a control computer for automated monitoring and response when threshold limits are not satisfied.

Turning now to the Figures, an embodiment of a stacking system 20 for stacking a plurality of cementitious boards 25 constructed according to principles of the present disclosure is shown in FIG. 1. In the illustrated embodiment, the stacking system 20 can be used at a dry end of a gypsum wallboard manufacturing line to place a plurality of cementitious boards 25 fed from a kiln (or other drier) in a stacked arrangement. In other embodiments, the stacking system can be used in conjunction with the stacking and edge hardness evaluation of other types of cementitious boards.

In the illustrated embodiment, each of the cementitious boards 25 has a cementitious core 27 interposed between a pair of cover sheets 28, 29. The cementitious core 27 is formed from an aqueous cementitious slurry. Each cementitious board 25 has first and second faces 31, 32 with a length extending along a longitudinal axis LA and a width extending along a transverse axis TA that is perpendicular to the longitudinal axis LA, and first and second edges 34, 35 with a thickness extending along a normal axis NA that is perpendicular to both the longitudinal axis LA and the transverse axis TA. The first and second edges 34, 35 extend along the longitudinal axis LA and are disposed in lateral spaced relationship to each other along the transverse axis TA. In the illustrated embodiment, the first face 31 of the cementitious boards 25 includes a pair of tapered portions 37, 38 respectively at the first and second edges 34, 35 such that each cementitious board 25 is asymmetrical about the transverse axis TA.

The aqueous cementitious slurry from which the cementitious core 27 of the cementitious boards 25 is formed can be produced at a suitably-configured wet end as will be readily understood by one skilled in the art. The wet end system can include any suitable equipment adapted to mix and/or assemble the constituent materials forming the cementitious board 25. In embodiments, the wet end system is configured as a gypsum wallboard wet end system.

In embodiments, the wet end system includes a cementitious slurry mixing and dispensing system, a forming table, and a forming station. The cementitious slurry mixing and dispensing system can have a slurry mixer in fluid communication with a slurry dispensing system. The slurry mixer is adapted to agitate water and a cementitious material (such as, calcined gypsum, for example) to form aqueous cementitious slurry, for example by including therein a rotor operable by a motor, shear pins, and other structure configured to impart further mixing action, as is readily appreciated by one skilled in the art. Any suitable mixer (e.g., a pin mixer) can be used with the slurry mixing and dispensing system. In embodiments, the mixer can be a suitable, commercially-available mixer, as is known in the gypsum board manufacturing art, such as, for example, one available from Gypsum Technologies Inc. or John Broeders Machine, both of Ontario, Canada.

Both the water and the cementitious material can be supplied to the mixer via one or more inlets as is known in the art. In embodiments, any other suitable slurry additive can be supplied to the mixer as is known in the art of manufacturing cementitious products. In use, water and a cementitious material, such as calcined gypsum, for example, can be agitated in the mixer to form aqueous cementitious slurry. In some embodiments, water and calcined gypsum can be continuously added to the mixer in a water-to-calcined gypsum ratio from about 0.5 to about 1.3, and in other embodiments of about 0.9 or less.

In embodiments, the slurry dispensing system can include a suitable discharge conduit, as is known in the art and examples of which are discussed in U.S. Pat. Nos. 6,494,609; 6,874,930; 7,007,914; and 7,296,919 and U.S. Patent Application Nos. 2012/0168527; 2012/0170403; 2013/0098268; 2013/0099027; 2013/0099418; 2013/0100759; 2013/0216717; 2013/0233880; and 2013/0308411, for example. The discharge conduit can be made from any suitable material and can have different shapes. In some embodiments, the discharge conduit can comprise a flexible conduit.

In embodiments, a foam injection system can be arranged with at least one of the mixer and the slurry dispensing system. The foam injection system can include a foam source (e.g., such as a foam generation system configured as known in the art) and a foam supply conduit. In embodiments, any suitable foam source can be used. Preferably, the aqueous foam is produced in a continuous manner in which a stream of a mix of foaming agent and water is directed to a foam generator, and a stream of the resultant aqueous foam leaves the generator and is directed to and mixed with the cementitious slurry. In embodiments, any suitable foaming agent can be used. Preferably, the aqueous foam is produced in a continuous manner in which a stream of the mix of foaming agent and water is directed to a foam generator, and a stream of the resultant aqueous foam leaves the generator and is directed to and mixed with the slurry. Some examples of suitable foaming agents are described in U.S. Pat. Nos. 5,683,635 and 5,643,510, for example.

A first roll of cover sheet material is configured to be selectively dispensed such that the first cover sheet 28 is dispensed from the first roll upstream of the slurry dispensing system and conveyed upon the forming table extending between the slurry mixer and dispensing system and the forming station. A second roll of cover sheet material is configured to be selectively dispensed such that the second cover sheet 29 is dispensed from the second roll upon the forming table at a position between the slurry dispensing system of the cementitious slurry mixing and dispensing system and the forming station over the first cover sheet 28 and the slurry dispensed from the slurry dispensing system. Gypsum board products are typically formed "front face down" such that the first cover sheet 28 dispensed from the first roll traveling over the forming table serves as the "front face" cover sheet 28 of the finished cementitious board 25 (which will be positioned toward an interior of a room when the cementitious boards 25 are installed).

In embodiments in which the cementitious slurry comprises gypsum slurry, one or both of the cover sheets 28, 29 can be pre-treated with a thin, relatively denser layer of gypsum slurry (relative to the gypsum slurry comprising the core), often referred to as a "skim coat" in the art, and/or hard edges, if desired. To that end, in embodiments, the mixer can include a first auxiliary conduit that is adapted to deposit a stream of dense aqueous cementitious slurry that is relatively denser than the main flow of aqueous calcined gypsum slurry delivered to the discharge conduit (i.e., a "face skim coat/hard edge stream").

In embodiments, a hard edge/face skim coat roller is disposed upstream of the slurry dispensing system of the cementitious slurry mixing and dispensing system and supported over the forming table such that the first cover sheet 28 being dispensed from the first roll is disposed therebetween. The first auxiliary conduit can deposit the face skim coat/hard edge stream upon the first cover sheet 28 being dispensed from the first roll upstream of the skim coat roller which is adapted to apply a skim coat layer to the moving first cover sheet 28 and to define hard edges at the periphery of the moving first cover sheet 28 by virtue of the width of the roller being less than the width of the moving first cover sheet 28 as is known in the art. Hard edges can be formed from the same dense slurry that forms the thin dense layer by directing portions of the dense slurry around the ends of the roller used to apply the dense layer to the first cover sheet 28.

In some embodiments, a back skim coat roller is disposed over a support element such that the second cover sheet 29 being dispensed from the second roll is disposed therebetween. The mixer can also include a second auxiliary conduit adapted to deposit a stream of dense aqueous calcined gypsum slurry that is relatively denser than the main flow of aqueous calcined gypsum slurry delivered to the discharge conduit (i.e., a "back skim coat stream"). The second auxiliary conduit can deposit the back skim coat stream upon the moving second cover sheet 29 upstream (in the direction of movement of the second cover sheet 29) of the back skim coat roller that is adapted to apply a skim coat layer to the second cover sheet 29 being dispensed from the second roll as is known in the art.

In other embodiments, separate auxiliary conduits can be connected to the mixer to deliver one or more separate edge streams to the moving cover sheet. Other suitable equipment (such as auxiliary mixers) can be provided in the auxiliary conduits to help make the slurry therein denser, such as by mechanically breaking up foam in the slurry and/or by chemically breaking up the foam through use of a suitable de-foaming agent inserted into the auxiliary conduit(s) through a suitable inlet.

The skim coat rollers, the forming table, and the other support elements can all comprise equipment suitable for their respective intended purposes as is known in the art. The wet end system can be equipped with other suitable equipment as is known in the art.

The wet end system, including the cementitious slurry mixing and dispensing system, the forming table, and the forming station, is configured to mix and assemble constituent materials together such that a continuous cementitious board 25 having a predetermined nominal thickness is fed from the forming station.

The forming station can be configured to form the cementitious board 25 such that the cementitious board 25 is within a predetermined thickness range to produce cementitious board of a given nominal thickness (e.g., ¼-in., ⅜-in., ½-in., and ⅝-in., for example). The forming station can comprise any equipment suitable for its intended purpose as is known in the art. For example, in embodiments, the forming station can include a pair of forming plates or rolls in spaced relationship to each other along the normal axis NA. The cementitious board 25 passes through the vertically spaced-apart forming plates/rolls to determine the thickness of the cementitious board 25. Equipment can be provided that helps wrap the front face cover sheet 28 around the sides of the sandwich to enclose the edges of the cementitious board 25, including applying an adhesive to secure the front face cover sheet 28 to the back cover sheet 29.

In embodiments, other cementitious board manufacturing stations, such as, a cutting station; a transfer system, including a board inverter; a dryer (or kiln); and a booking unit, for example, can be interposed between the forming station and the stacking system 20. The cutting station can be situated a sufficient distance away from the forming station to allow the cementitious slurry constituting the cementitious core 27 to adequately set before reaching the cutting station such that the cementitious board 25 can be cut cleanly. The cutting station can include a knife configured to periodically cut the cementitious board 25 along the transverse axis TA to define a series of board segments as the cementitious board 25 moves past the cutting station. In embodiments, the knife can be a rotary knife as is generally known to those skilled in the art. The transfer system can be configured to flip the cementitious boards 25 over such that the boards are sent through the kiln (drier) in a front face up position.

The kiln can be configured to provide an environment with an elevated temperature sufficient to drive off free water in the cementitious board that is not otherwise used in the chemical hydration reaction occurring in the aqueous cementitious slurry forming the core of the cementitious board 25. In embodiments, the kiln (drier) can comprise any suitable equipment as known to those skilled in the art.

In embodiments, a suitable booking unit can be interposed between the kiln and the stacking system 20. The booking unit can be configured to place a pair 40 of boards together in a "booked" relationship in which the front faces 31 of the pair 40 of booked cementitious boards are mated together with the pair of boards being in a stacked relationship. In embodiments, the booking unit can comprise any suitable equipment as known to those skilled in the art. One skilled in the art will understand that other equipment and/or manufacturing stations can be included in embodiments of a cementitious board manufacturing line suitable for producing cementitious board which can be evaluated according to principles of the present disclosure.

Referring to FIG. 1, the illustrated stacking system 20 includes a lift assembly 50, a conveyor 52, a backstop member 54, and a system 55 for determining an edge hardness value of cementitious boards 25 constructed according to principles of the present disclosure. In embodiments, the stacking system 20 can include other components and equipment, as one skilled in the art will appreciate. For example, in embodiments, the stacking system 20 can include patting members fitted to suitable actuators to pat the stack of cementitious boards along the longitudinal axis LA and/or the transverses axis TA to maintain the alignment of the stack of cementitious boards 25 as more cementitious boards 25 are added to the stack.

The lift assembly 50 is configured to support the cementitious boards 25 in a stacked arrangement upon a support surface 70. The illustrated lift assembly 50 includes a support fixture 72 and a hoist 74. The support fixture 72 includes the support surface 70 which is configured to support the cementitious boards 25 such that the first and second faces 31, 32 of the cementitious boards 25 are generally parallel to the support surface 70. In embodiments, the support surface 70 can be formed from any suitable structure, including a platform or a series of accumulator arms as will be appreciated by one skilled in the art.

The hoist 74 is connected to the support fixture 72 and is adapted to move the support fixture (along with the support surface 70) over a range of travel along the normal axis NA. In embodiments, the hoist 74 can be any suitable type of mechanism that can selectively raise and lower the support fixture 72 along the normal axis NA. In the illustrated embodiment, the hoist 74 comprises a scissors-lift mechanism with multiple pairs of braces in an X-configuration that can be pivoted about a center connection point (via a suitable actuator) to raise and lower the support fixture. In other embodiments, the hoist can include linear actuators with threaded screws or any other suitable lift equipment known to those skilled in the art.

The conveyor 52 is configured to serially convey the cementitious boards 25 to a position over the lift assembly 50 for being placed upon the support surface 70. In embodiments, the conveyor 52 can comprise any equipment suitable for its intended purpose as is known in the art. In the illustrated embodiment, the conveyor 52 includes a plurality of support members 77 that comprise rollers journaled for rotation. In embodiments, at least a portion of the conveyor 52 can be equipped with a belt formed as an endless loop. In yet other embodiments, the conveyor 52 can include pick equipment (such as a vacuum-assist device) to facilitate the placement of the cementitious boards 25 over the lift assembly 50. In the illustrated embodiment, the conveyor is configured to transport the cementitious boards 25 along a conveying direction 79 with the transverse axis TA of the cementitious boards 25 being aligned with the conveying direction 79. In other embodiments, the conveyor (and the other equipment of the stacking system 20) can be configured to transport the cementitious boards 25 to the lift assembly with the longitudinal axis LA of the boards 25 being aligned with the conveying direction 79.

The backstop member 54 is positioned to stop the cementitious boards 25 from being moved via the conveyor 52 such that the cementitious boards 25 are serially stopped at a position over the support surface 70 of the lift assembly 50. In embodiments, the location of the backstop member 54 can be adjusted along at least one axis in order to place the backstop member 54 in contacting engagement with the cementitious boards 25 being dispensed from the conveyor 52 and/or to accommodate cementitious boards of different sizes (e.g., different widths along the transverse axis TA) while stile arresting their movement over the support surface 70 of the lift assembly 50. In the illustrated embodiment, the edge hardness measurement system 55 is mounted to the backstop member 54.

In embodiments, the operation of the conveyor 52 and the lift assembly 50 can be orchestrated using any suitable control system known to those skilled in the art. In embodiments, the lift assembly 50 can indexingly lower the height of the support surface 70 along the normal axis 50 (by the thickness of the pair 40) as each pair 40 of booked cementitious boards is fed from the conveyor 52 upon the growing stack of cementitious boards upon the lift assembly. Once the stack of cementitious boards 25 is removed from the lift assembly 50, the height of the support surface 70 can be raised along the normal axis NA back to a position in which the support surface 70 is substantially coplanar with the top of the conveyor 52, and the stacking sequence can occur again.

The edge hardness measurement system 55 is configured to measure an edge hardness value of the cementitious board 25 with which it is associated. In embodiments, the edge hardness measurement system 55 is configured to be an automated test instrument to provide a measurement of an edge hardness characteristic (e.g., hardness and/or compression strength) of the cementitious board 25 after it has dried. The illustrated edge hardness measurement system 55 is disposed downstream of the kiln (drier) at the stacking station.

In embodiments, the edge hardness measurement system 55 can be located at a variety of other locations along the cementitious board manufacturing line or at another site. In embodiments, the measurement position of the edge hardness measurement system 55 is located sufficiently downstream of the cementitious board manufacturing line such that the hydration reaction of the aqueous cementitious slurry forming the core 27 of the cementitious board 25 is substantially completed by the time that portion of the cementitious board 25 reaches the measurement position.

Figure 2:
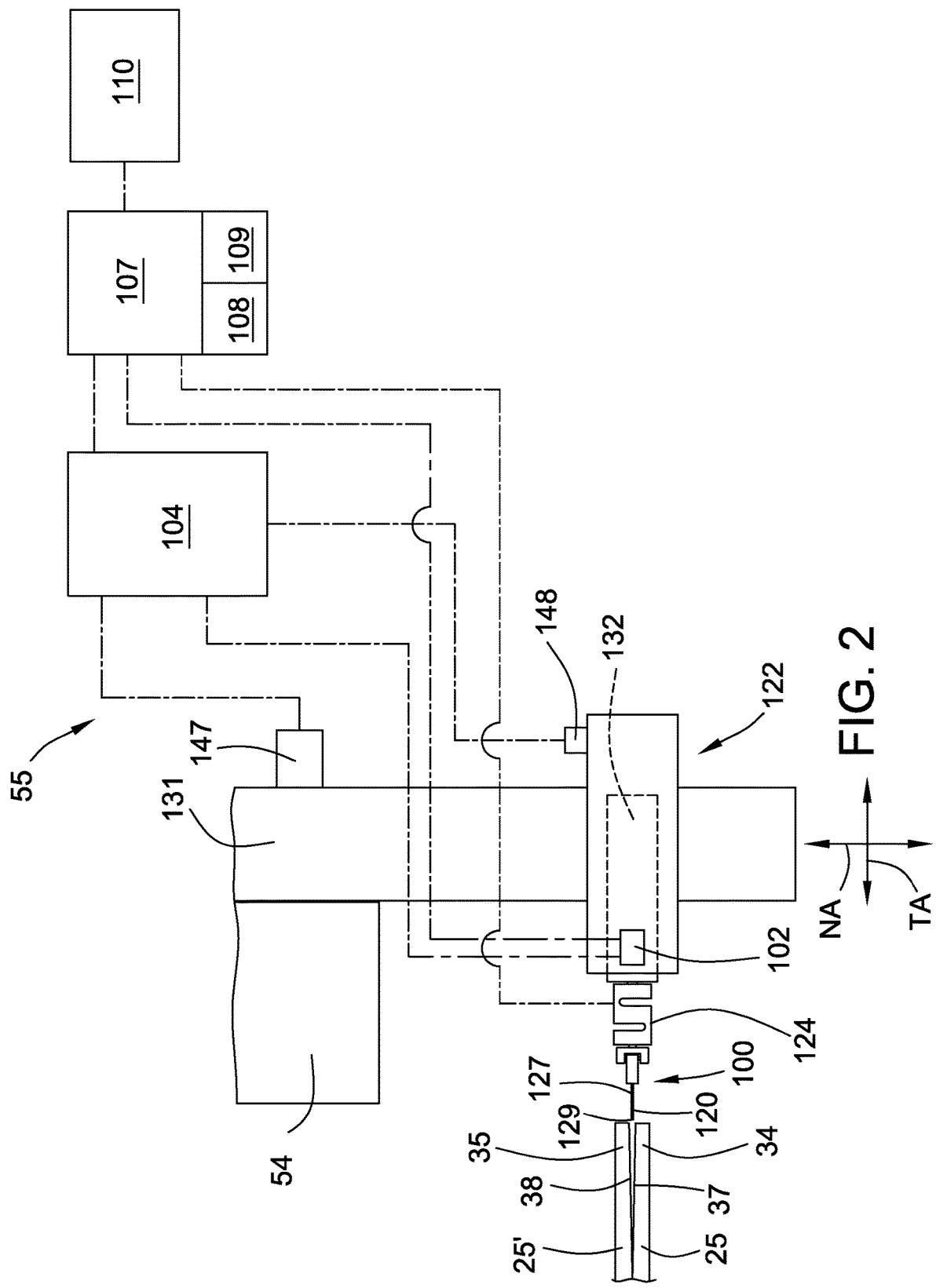
FIG. 2 is a fragmentary, schematic, enlarged detail view of the system for determining cementitious board edge hardness of FIG. 1.

In embodiments, the edge hardness measurement system 55 can comprise any suitable device configured to generate resistance force data by compressively penetrating the cementitious board 25 in a controlled, automated manner at a designated location. Referring to FIGS. 1 and 2, the illustrated embodiment of the edge hardness measurement system 55 includes the support fixture 72, a punch assembly 100, a board detection device 102, a controller 104, a processor 107, a non-transitory computer readable medium 108 bearing an edge hardness measurement program, a data storage device 109, and a display device 110.

In the illustrated embodiment, the support fixture 72 of the lift assembly comprises the support fixture of the edge hardness measurement system 55 comprises and includes the support surface 70 which is configured to support the cementitious board 25. In other embodiments, the support fixture and its support surface 72 can have a different configuration.

The illustrated punch assembly 100 includes a punch 120, an actuator assembly 122, and a force gauge 124. The punch 120 has a cylindrical distal portion 127 with a distal end 129 (see FIG. 2).

The actuator assembly 122 includes a first actuator 131 and a second actuator 132. The first actuator 131 is configured to move the punch 120 along the normal axis NA relative to the cementitious board 25 supported in the support fixture to adjust the position of the punch 120 relative to the thickness of the cementitious board 25. The second actuator 132 supports the punch 120. The second actuator 132 is configured to move the punch 120 along the transverse axis TA relative to the cementitious board 25 supported in the support fixture 72 to adjust the position of the punch 120 relative to the width of the cementitious board 125. The second actuator 132 is configured to reciprocally move the punch 120 along the transverse axis TA over a measurement stroke between a home position (see FIG. 3) and a measurement position (see FIG. 4). When the punch 120 is in the home position, the distal end 129 of the punch 120 is in offset relationship to the cementitious board 25 supported in the support fixture 72. When the punch 120 is in the measurement location, the distal end 129 of the punch 120 is in interfering relationship with the cementitious board 25 supported in the support fixture 72. Accordingly, the first actuator 131 is configured to align the punch 120 along the normal axis NA within the thickness of the cementitious board 25 (and substantially equidistant along the normal axis NA) between the front and back faces 31, 32), and, so aligned, the second actuator 132 is configured to drive the distal end 129 of the punch 120 into one of the first and second edges 34, 35 of the cementitious board 25 supported in the support fixture 72 when the punch 120 moves from the home position to the measurement position.

The force gauge 124 is supported by the second actuator 132 of the actuator assembly 122 and is interposed between the punch 120 and the second actuator 132. The force gauge 124 is configured to measure a resistance force exerted against the punch 120 by the cementitious board 125 being tested in response to the distal end 129 of the punch 120 being inserted into the edge 34, 35 of the cementitious board 25. The force gauge 124 is configured to generate a force signal indicative of the resistance force.

The processor 107 is in communication with the force gauge 124 to receive the force signal therefrom. The processor 107 is programmed with an edge hardness measurement program stored on the non-transitory computer readable medium 108. The edge hardness measurement program is configured to use the force signal to determine the edge hardness value for the cementitious board.

In embodiments, the punch 120 can be substantially aligned along the normal axis NA with a support member (such as a squaring member or suitable backstop member, e.g.) positioned against the edge 34, 35 of the cementitious board 25 in opposing relationship to the one being tested. The support member can help support the cementitious board 25 to help prevent the cementitious board 25 from moving laterally along the transverse axis TA when the punch 120 engages it, thereby facilitating the penetration of the board 25 by the punch 120 and helping prevent the punch 120 from damaging the cementitious board 25 (e.g., cracking or tearing the cementitious board 25) to the extent that the board 25 would be considered to have a defect preventing its sale. In embodiments, the punch 120 can be positioned along the normal axis NA with respect to the stacked cementitious boards 28 upon the lift assembly 50 such that the weight of the cementitious boards 25 above the one being tested helps prevent the relative lateral movement of the cementitious board 25 being tested during the measurement stroke of the punch 120.

In the illustrated embodiment, the punch 120 is made from steel in accordance with ASTM Standard C473-16. In embodiments, the distal portion 127 of the steel punch is 0.099±0.003 in. (2.515±0.076 mm) in diameter and is at least ½ in. (12.7 mm) long with the bearing surface of the distal end 129 being machined to a 90° angle in reference (in accordance with ASTM Standard C473-16). In other embodiments, the punch 120 can have a different configuration.

Referring to FIG. 3, in the illustrated embodiment, the edge hardness measurement system 55 includes a punch mounting assembly 140 for supporting the punch 120. The punch mounting assembly 140 is configured to secure the punch 120 to the actuator assembly 122 via the force gauge 124 so that the center axis of the punch 120 is parallel with its line of travel over the measurement stroke (in accordance with ASTM Standard C473-16). The punch mounting assembly 140 includes a mounting bracket 142 and a pin 144. The mounting bracket 142 can be secured to the force gauge 124, and the punch 120 can be secured to the mounting bracket 142 via the pin 144. In other embodiments, the punch 120 can have a different mounting arrangement.

Referring to FIG. 2, the actuator assembly 122 can be configured to operate, in response to receiving a command signal from the controller 104, to selectively place the punch 120 in inserted contact with the cementitious board 25 to measure an edge hardness set characteristic of the cementitious board 25. In the illustrated embodiment, each of the first actuator 131 and the second actuator 132 of the actuator assembly 122 includes a linear actuator power source 147, 148. In embodiments, the first and second actuators 131, 132 can comprise any suitable linear actuator equipment suitable for selectively moving the punch 120 over a range of travel along the normal axis NA and along the transverse axis between a home position (see FIG. 3) and a measurement position (see, e.g., FIG. 4) and to deliver a sufficient force to insert the punch 120 into the edge of the cementitious board 25 being tested by a predetermined amount. For example, in embodiments, the second actuator 132 is configured to move the distal end 129 of the punch a distance of ⅝-in. along the transverse axis TA when moving from the home position to the measurement position. In other embodiments, the distance of the measurement stroke can be varied.

The linear actuator power sources 147, 148 are configured to selectively and independently operate the first and second actuators 131, 132, respectively. The linear actuator power sources 147, 148 are in operable communication with the controller 104.

In embodiments, the first and second actuators 131, 132 can be configured to move the punch 120 with respect to the cementitious board being tested in a controlled manner. For example, in embodiments, the first and second actuators 131, 132 can be equipped with an encoder to help move the punch 120 to a designated location along the normal axis NA and along the transverse axis TA, respectively.

The force gauge 124 can be configured to transmit the resistance force data it obtains to the processor 107. The processor 1078, in turn, is configured to use the resistance force data to determine an edge hardness characteristic for the cementitious board 25 being tested. The illustrated force gauge 124 comprises a compression type strain gauge load cell. In embodiments, the force gauge 124 can comprise any suitable device configured to measure the resistance force generated by the cementitious board 25 in response to the punch 120 being inserted into one of its edges. In the illustrated embodiment, the force gauge 124 is interposed between the punch 120 and the second actuator 132 of the actuator assembly 122. In embodiments, the force gauge 124 can have any suitable measurement range (e.g., capable of measuring compression forces up to approximately 100 pounds).

In embodiments, the board detection system 102 is configured to sense the edges of the board 25, determine the board thickness, determine which edge of the board is adjacent the punch 120 for edge hardness testing, and to indicate a center point between a pair of booked cementitious boards to begin an edge hardness testing sequence of both booked boards. In the illustrated embodiment, the board detection system 102 comprises a laser distance gauge. The laser distance gauge 102 is connected to the body of the second actuator 132 such that it is suspended in a fixed position along the transverse axis TA (but is movable along the normal axis NA when the first actuator 1331 is operated). In embodiments, other equipment suitable for carrying out one or more of the detection functions described herein can be used. For example, in embodiments, the board detection system 102 is in the form of a vision system. In embodiments, any suitable commercially-available vision system can be used, such as, a commercially-available 3D vision system, for example.

In embodiments, the board detection system 102 is configured to detect the position along the normal axis NA of the cementitious board 25 supported in the support fixture 72 that is being tested. The board detection system 102 can be configured to generate a board position signal indicative of the position along the normal axis NA of the cementitious board 25 being tested.

The controller 104 is in communication with the board detection system 102 to receive the board position signal therefrom. The controller 104 can be configured to selectively operate the first actuator 131 of the actuator assembly 122 based upon the board position signal to move the punch 120 along the normal axis NA (either up or down) to position the punch 120 along the normal axis NA within the thickness of the cementitious board 25 being tested. In embodiments, the controller 104 places the punch 120 substantially equidistant along the normal axis NA between the front and back faces 31, 32 of the cementitious board 25 being tested.

In embodiments, the board detection system 102 is configured to detect the orientation of the first and second edges 34, 35 of the cementitious board 25 supported in the support fixture 72 which is being tested relative to the punch 120. The board detection system 102 can be configured to generate a board orientation signal indicative of the orientation of the first and second edges 34, 35 of the cementitious board 25 with respect to the punch 120 to indicate which of the first and second edges 34, 35 of the cementitious board 25 being tested the punch 120 is inserted into when the punch 120 moves from the home position to the measurement position.

For example, in the illustrated embodiment which is being used to test cementitious boards 25 having tapered portions 37, 38 along its front face 31, the board detection system 102 can be configured to detect the location of the tapered portion of a given board along the normal axis NA to determine whether that board 25 is oriented front-face up or front-face down (and correspondingly which of the first and second edges 34, 35 is adjacent the punch 120). Referring to FIG. 3, the lower cementitious board 25 has its tapered portion 37 located closest to the punch 120 and it is located at the upper part of the board 25 as it is stacked. Accordingly, the board detection system 102 can be configured to generate a board orientation signal indicating the first edge 34 of the board 25 is closer to the punch. The upper cementitious board 25' has its tapered portion 38 located closest to the punch 120 and it is located at the lower part of the board 25' as it is stacked. Accordingly, the board detection system 102 can be configured to generate a board orientation signal indicating the second edge 35 of the board 25' is closer to the punch 120.

In embodiments, the board detection system 102 is configured to detect a center position along the normal axis NA between a pair of booked cementitious boards 25, 25' supported by the support fixture, as shown in FIG. 3. The booked cementitious boards 25, 25' are in contacting relationship with each other such that the first edge 34 of one cementitious board 25 is aligned with the second edge 35 of the other cementitious board 25', and the position signal the board detection system 102 is configured to generate is a booked pair position signal indicative of the center position along the normal axis NA of the pair of booked cementitious boards 25, 25'.

The controller 104 is in communication with the board detection system 102 to receive the booked pair position signal therefrom. In response, the controller 104 can be configured to serially move through a sequence of hard edge measurements. The controller 104 can operate the first actuator 131 of the actuator assembly 122 based upon the booked pair position signal to move the punch 120 along the normal axis NA to position the punch 120 in a first pair position along the normal axis NA within the thickness of one of the pair of booked cementitious boards 25, as shown in FIG. 4.

The controller 104 can operate the second actuator 132 of the actuator assembly 122 to reciprocally move the punch 120 along the transverse axis TA over the measurement stroke to test the first cementitious board 25. The force gauge 124 can transmit the force signal to the processor 107 so that the edge hardness value for the first edge 34 of the first cementitious board 25 can be determined.

The controller 104 can then operate the first actuator 131 of the actuator assembly 122 based upon the booked pair position signal to move the punch 120 along the normal axis NA to position the punch 120 in a second pair position along the normal axis NA within the thickness of the other of the pair of booked cementitious boards 25'. The controller 104 can operate the second actuator 132 of the actuator assembly 122 to reciprocally move the punch 120 along the transverse axis TA over the measurement stroke to test the second cementitious board 25'. The force gauge 124 can transmit the force signal to the processor 107 so that the edge hardness value for the second edge 35 of the second cementitious board 25' can be determined. After each measurement, the controller 104 retracts the punch 120 back to the home position such that the punch 120 is clear of the stack of cementitious board 25 before the controller 104 operates the first actuator 131 to adjust the height of the punch 120 along the normal axis NA.

The processor 107 is in operable arrangement with the board detection system 102 to receive the board position and orientation data therefrom. The edge hardness measurement program can include a board position analysis module configured to convert the data received from the board detection system 102 to record which edge of the board was tested (and when the data, including the force resistance data, was taken) in real time in a database contained in the data storage device 109.

Referring to FIG. 2, the controller 104 is in operable arrangement with the punch assembly 100, the board detection system 102, and the processor 107. In embodiments, the controller 104 is configured to selectively operate the punch assembly 100 to generate resistance force data corresponding to an edge hardness of the cementitious board 25 being tested.

The controller 104 is in operable arrangement with the actuator assembly 122. In particular in the illustrated embodiment, the controller 104 is in operable arrangement with the linear actuator power sources 147, 148 of the actuator assembly 122. The controller 104 can be configured to selectively and independently operate the actuator power sources 147, 148 to move the punch 120 along the normal axis NA and the transverse axis TA, respectively. The controller 104 can be configured to selectively operate the actuator power source 147 of the first actuator 131 to move the punch 120 along the normal axis NA to position the punch 120 within the thickness of a selected one of the cementitious boards 25 in the stack of boards resting upon the lift assembly 50. The controller 104 can be configured to selectively operate the actuator power source 148 of the second actuator 132 to move the punch 120 along the transverse axis TA to perform a measurement stroke to take an edge hardness measurement. The controller 104 is configured to selectively operate the second actuator 132 of the actuator assembly 122 to reciprocally move the punch 120 along the transverse axis TA over the measurement stroke. In embodiments, the controller 104 can be configured to operate the actuator assembly 122 to perform an edge hardness measurement in response to a command signal and/or after a set period of time has elapsed (or a certain number of boards 25 have been stacked upon the lift assembly 50).

In embodiments, the controller 104 can include a user input and/or interface device having one or more user actuated mechanisms (e.g., one or more push buttons, slide bars, rotatable knobs, a keyboard, and a mouse) adapted to generate one or more user actuated input control signals. In embodiments, the controller 104 can be configured to include one or more other user-activated mechanisms to provide various other control functions for the slurry set measurement system, as will be appreciated by one skilled in the art. The controller 104 can include a display device adapted to display a graphical user interface. The graphical user interface can be configured to function as both a user input device and a display device in embodiments. In embodiments, the display device can comprise a touch screen device adapted to receive input signals from a user touching different parts of the display screen. In embodiments, the controller 104 can be in the form of a smart phone, a tablet, a personal digital assistant (e.g., a wireless, mobile device), a laptop computer, a desktop computer, or other type of device. In embodiments, the controller 104 and the processor 107 can comprise the same device or set of equipment.

In embodiments, the processor 107 comprises a specially programmed processor that can be used to determine the edge hardness of the cementitious board being tested based upon the resistance force data sent to the processor 107 by the force gauge 124. In the illustrated embodiment, the processor 107 is in operable arrangement with the controller 104 to facilitate the control and the operation of the edge hardness measurement system 55. The processor 107 can be configured to receive input signals from the controller 104, to send input control signals to the controller 104, and/or to send output information to the controller 104. The processor 107 is in operable arrangement with the force gauge 124 to receive the resistance force data therefrom and with the board detection system 102 to receive board position and orientation data therefrom. The processor 107 is in operable arrangement with the non-transitory computer-readable medium 108 to execute the edge hardness measurement program contained thereon. The processor 107 is in operable arrangement with the display device 110 to selectively display output information from the edge hardness measurement program and/or to receive input information from a graphical user interface displayed by the display device 110.

In embodiments, the processor 107 is configured to display the resistance force data received from the punch assembly 100 in the display device 110. The resistance force data can also be stored in the data storage device 109 operably arranged with the processor 107, and/or to correlate the resistance force data with a board set characteristic, such as, its edge hardness and/or its compressive strength.

In embodiments, the processor 107 can comprise any suitable computing device, such as, a microprocessor, a mainframe computer, a digital signal processor, a portable computing device, a personal organizer, a device controller, a logic device (e.g., a programmable logic device configured to perform processing functions), a digital signal processing (DSP) device, or a computational engine within an appliance. In embodiments, the processor 107 also includes one or more additional input devices (e.g., a keyboard and a mouse).

The processor 107 can have one or more memory devices associated therewith to store data and information. The one or more memory devices can include any suitable type, including volatile and non-volatile memory devices, such as RAM (Random Access Memory), ROM (Read-Only Memory), EEPROM (Electrically-Erasable Programmable Read-Only Memory), flash memory, etc. In one embodiment, the processor 107 is adapted to execute programming stored upon a non-transitory computer readable medium to perform various methods, processes, and modes of operations in a manner following principles of the present disclosure.

The edge hardness measurement program is configured to calculate the edge hardness value based upon the force signal received by the processor 107 from the force gauge 124. In embodiments, the edge hardness measurement program is configured to use a peak load of the resistance force measured by the force gauge 124 as the punch 120 moves from the home position to the measurement position to calculate the edge hardness. In embodiments, the peak load can be expressed in pounds-force or Newtons, for example.

In embodiments, the non-transitory computer readable medium 108 can contain an edge hardness measurement program that is configured to implement an embodiment of a method of determining an edge hardness value of a cementitious board according to principles of the present disclosure. In embodiments, the edge hardness measurement program includes a graphical user interface that can be displayed by the display device 110. The graphical user interface can be used to facilitate the inputting of commands and data by a user to the edge hardness measurement program and to display outputs generated by the edge hardness measurement program.

The edge hardness measurement program can be stored upon any suitable computer-readable storage medium. For example, in embodiments, an edge hardness measurement program following principles of the present disclosure can be stored upon a hard drive, floppy disk, CD-ROM drive, tape drive, zip drive, flash drive, optical storage device, magnetic storage device, and the like.

In embodiments, the edge hardness measurement program is configured to use the force signal transmitted from the force gauge 124 to determine a set characteristic of the aqueous cementitious slurry forming the core 27 of the cementitious board 25. In embodiments, the resistance force data (or a correlated characteristic, such as edge hardness) can be displayed by the edge hardness measurement program via the graphical user interface in the display device 110. In embodiments, an operator can set a predetermined tolerance range for the resistance force (or a correlated board characteristic, include edge hardness), and the edge hardness measurement program can be configured to operate an alarm if the resistance force (or a correlated board characteristic) falls outside of the tolerance range. In embodiments, the alarm can be any suitable alarm including an audible signal and/or a warning message displayed via the graphical user interface on the display device 110.

In embodiments, the processor 107 is in operable communication with the data storage device 109 which includes at least one database containing board characteristic data. In embodiments, the edge hardness measurement program can be configured to store the resistance force data generated by the punch assembly 100 and the board position and orientation data generated by the board detection system 102 in the data storage device 109. In embodiments, the resistance force data, board position and orientation data, and time data for a given measurement can be associated in a logical manner in the data storage device such that the various data can be retrievable for a given measurement.

Figure 6:
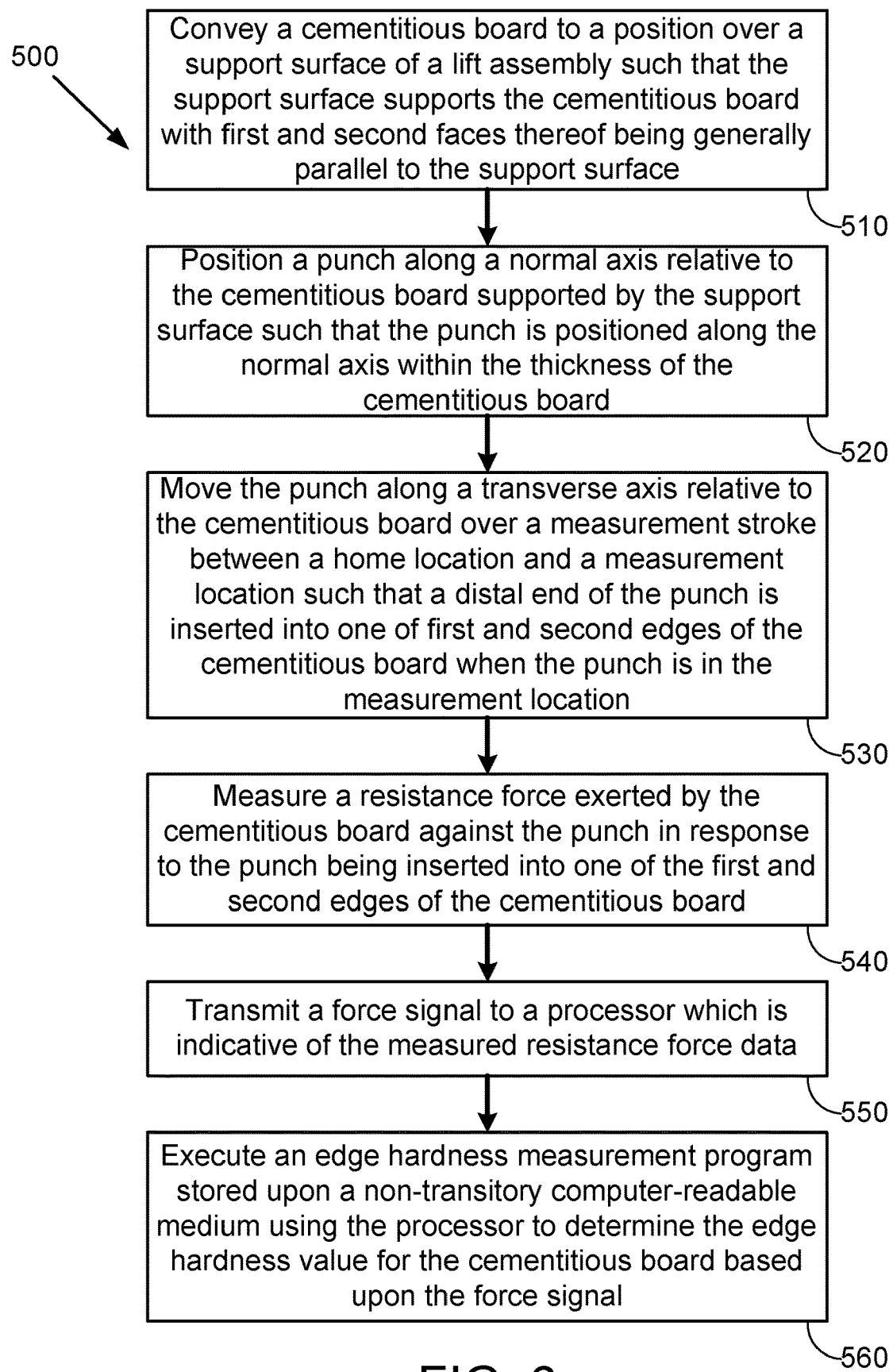
FIG. 6 is a flowchart illustrating steps of an embodiment of method of determining an edge hardness value of a cementitious board following principles of the present disclosure.

Referring to FIG. 6, steps of an embodiment of a method 500 of determining an edge hardness value of a cementitious board following principles of the present disclosure are shown. In embodiments, a method of determining an edge hardness value of a cementitious board following principles of the present disclosure can be used with any embodiment of a system for determining an edge hardness value of a cementitious board according to principles discussed herein.

The illustrated method 500 of determining an edge hardness value of a cementitious board with a cementitious board that has a cementitious core formed from aqueous cementitious slurry, first and second faces with a length extending along a longitudinal axis and a width extending along a transverse axis that is perpendicular to the longitudinal axis, and first and second edges with a thickness extending along a normal axis that is perpendicular to both the longitudinal axis and the transverse axis. The illustrated method 500 includes conveying the cementitious board to a position over a support surface of a lift assembly such that the support surface supports the cementitious board with the first and second faces being generally parallel to the support surface (step 510). A punch is positioned along the normal axis relative to the cementitious board supported by the support surface such that the punch is positioned along the normal axis within the thickness of the cementitious board (step 520). The punch is moved along the transverse axis relative to the cementitious board supported by the support surface over a measurement stroke between a home position, in which a distal end of the punch is in offset relationship to the cementitious board, and a measurement position, in which the distal end of the punch is in interfering relationship with the cementitious board, such that the distal end of the punch is inserted into one of the first and second edges of said cementitious board when the punch is in the measurement position (step 530).

A resistance force, which is exerted by the cementitious board against the punch in response to the punch being inserted into one of the first and second edges of said cementitious board, is measured (step 540). The force signal is transmitted to a processor (step 550). The force signal is indicative of the measured resistance force.

An edge hardness measurement program stored upon a non-transitory computer-readable medium is executed using the processor to determine the edge hardness value for the cementitious board based upon the force signal (step 560). In embodiments, the edge hardness measurement program calculates the edge hardness value based upon a peak load of the measured resistance force as the punch moves from the home position to the measurement position.

In embodiments of a method of determining an edge hardness value of a cementitious board following principles of the present disclosure, the edge hardness value is displayed in a display device arranged with the processor via a graphical user interface. In embodiments, the edge hardness measurement program is configured to compare the edge hardness value to a predetermined edge hardness value range and issue an alert via the graphical user interface when the calculated edge hardness value falls outside of the selected edge hardness value range.

In embodiments of a method of determining an edge hardness value of a cementitious board following principles of the present disclosure, the first face of the cementitious board includes a pair of tapered portions respectively adjacent the first and second edges such that each cementitious board is asymmetrical about the transverse axis. The method 500 can further include detecting the orientation of the first and second edges of the cementitious board supported by the support surface relative to the punch. A board orientation signal is transmitted to the processor. The board orientation signal is indicative of the orientation of the first and second edges of the cementitious board with respect to the punch to indicate into which one of the first and second edges the punch was inserted.

In embodiments of a method of determining an edge hardness value of a cementitious board following principles of the present disclosure, the method 500 can include lowering the support surface of the lift assembly relative to a conveyor along the normal axis. A pair of booked cementitious boards is conveyed to the position over the support surface of the lift assembly such that the support surface supports the pair of booked cementitious boards in a stacked arrangement upon the support surface. In embodiments, the position is detected along the normal axis of one of the cementitious boards in the stacked arrangement upon the support surface. A board position signal is transmitted to a controller. The board position signal is indicative of the position of that cementitious board along the normal axis. The controller is used to move the punch along the normal axis based upon the board position signal to position the punch along the normal axis within the thickness of that cementitious board.

In embodiments, the first face of each of the pair of booked cementitious boards includes a pair of tapered portions respectively adjacent the first and second edges such that each of the booked cementitious boards is asymmetrical about the transverse axis. The pair of booked cementitious boards is in contacting relationship with each other such that the first edge of one cementitious board is aligned with the second edge of the other cementitious board.

In embodiments of a method of determining an edge hardness value of a cementitious board following principles of the present disclosure, the method 500 can include detecting a center position along the normal axis between the pair of booked cementitious boards supported by the support fixture. A booked pair position signal is transmitted to a controller. The booked pair position signal is indicative of the center position along the normal axis of the pair of booked cementitious boards.

The orientation is detected of the first and second edges of the pair of booked cementitious boards supported by the support surface relative to the punch. A board orientation signal is transmitted to the processor. The board orientation signal is indicative of the orientation of the first and second edges of the pair of booked cementitious boards with respect to the punch.

The controller is used to move the punch along the normal axis based upon the booked pair position signal to position the punch in a first pair position along the normal axis within the thickness of a first one of the pair of booked cementitious boards having the first edge adjacent the punch. The punch is reciprocally moved along the transverse axis over the measurement stroke for a first edge hardness measurement of the first edge of the first one of the pair of booked cementitious boards. The resistance force exerted by the first one of the pair of booked cementitious boards against the punch in response to the punch being inserted into the first edge of the first one of the pair of booked cementitious boards is measured. The force signal relating to the first edge hardness measurement, which is indicative of the measured resistance force for the first edge hardness measurement, is transmitted to the processor.

The controller is used to move the punch along the normal axis based upon the booked pair position signal to position the punch in a second pair position along the normal axis within the thickness of the other one of the pair of booked cementitious boards having the second edge adjacent the punch. The punch is reciprocally moved along the transverse axis over the measurement stroke for a second edge hardness measurement of the second edge of the other one of the pair of booked cementitious boards. The resistance force exerted by the other one of the pair of booked cementitious boards against the punch in response to the punch being inserted into the second edge of the other cementitious board is measured. The force signal relating to the second edge hardness measurement, indicative of the measured resistance force for the second edge hardness measurement, is transmitted to the processor.

In embodiments of a method of determining an edge hardness value of a cementitious board following principles of the present disclosure, executing the edge hardness measurement program stored upon the non-transitory computer-readable medium using the processor includes displaying, through a graphical user interface, the edge hardness value determined for the cementitious boards for which a measurement was taken. In embodiments, an operator may use the measured resistance force (expressed in pounds-force or Newtons, e.g.) directly as a numerical value relating to edge hardness which can be displayed through the graphical user interface in the display device. In embodiments, the edge hardness measurement program can be configured to display through the graphical user interface the peak load measured by the force gauge during the measurement stroke. In embodiments, the edge hardness measurement program can be in operable relationship with a data storage device configured to receive resistance force data, measurement stroke data, edge testing data (e.g., which edge of the board was tested during a particular measurement) and time data (e.g., at what time and date was the measurement taken).

In embodiments of a method of determining an edge hardness value of a cementitious board following principles of the present disclosure, the controller can be used to take an edge hardness measurement of the cementitious board with which the punch is arranged in response to the controller receiving a command signal and/or according to a predetermined time interval and/or number of boards stacked in the stacker. In embodiments, the interval between edge hardness measurements can be varied.

All references cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A system for determining an edge hardness value of a cementitious board, the cementitious board having a cementitious core formed from aqueous cementitious slurry, the cementitious board having first and second faces with a length extending along a longitudinal axis and a width extending along a transverse axis that is perpendicular to the longitudinal axis, and first and second edges with a thickness extending along a normal axis that is perpendicular to both the longitudinal axis and the transverse axis, the system comprising:
    a support fixture, the support fixture having a support surface configured to support the cementitious board such that the first and second faces are generally parallel to the support surface;
    a punch, the punch having a distal portion with a distal end, the distal portion being cylindrical;
    an actuator assembly, the actuator assembly including a first actuator and a second actuator, the second actuator supporting the punch, the first actuator being configured to move the punch along the normal axis relative to the cementitious board supported in the support fixture to adjust a normal position of the punch relative to the thickness of the cementitious board, and the second actuator being configured to move the punch along the transverse axis relative to the cementitious board supported in the support fixture to adjust a transverse position of the punch relative to the width of the cementitious board, the second actuator being configured to reciprocally move the punch along the transverse axis over a measurement stroke between a home position, in which the distal end of the punch is in offset relationship to the cementitious board supported in the support fixture, and a measurement position, in which the distal end of the punch is in interfering relationship with the cementitious board supported in the support fixture, such that the second actuator is configured to drive the distal end of the punch into one of the first and second edges of the cementitious board supported in the support fixture when the punch moves from the home position to the measurement position;
    a force gauge, the force gauge supported by the second actuator of the actuator assembly and interposed between the punch and the second actuator, the force gauge configured to measure a resistance force exerted against the punch by the cementitious board in response to the distal end of the punch being inserted into the edge of the cementitious board, the force gauge configured to generate a force signal indicative of the resistance force;
    a processor, the processor in communication with the force gauge to receive the force signal therefrom, the processor programmed with an edge hardness measurement program stored on a non-transitory computer readable medium, the edge hardness measurement program being configured to use the force signal to determine the edge hardness value for the cementitious board.

2. The system according to claim 1, wherein the edge hardness measurement program is configured to determine the edge hardness value based upon a peak load of the resistance force measured by the force gauge as the punch moves from the home position to the measurement position.

3. The system according to claim 1, further comprising:
    a controller, the controller being in operable arrangement with the actuator assembly, the controller configured to selectively operate the second actuator of the actuator assembly to reciprocally move the punch along the transverse axis over the measurement stroke.

4. The system according to claim 3, further comprising:
    a board detection system, the board detection system being configured to detect the position of the cementitious board supported in the support fixture along the normal axis, the board detection system configured to generate a board position signal indicative of the position of the cementitious board along the normal axis;
    wherein the controller is in communication with the board detection system to receive the board position signal therefrom, the controller configured to selectively operate the first actuator of the actuator assembly based upon the board position signal to move the punch along the normal axis to position the punch along the normal axis within the thickness of the cementitious board.

5. A stacking system for stacking a plurality of cementitious boards, each cementitious board having a cementitious core formed from an aqueous cementitious slurry, the cementitious board having first and second faces with a length extending along a longitudinal axis and a width extending along a transverse axis that is perpendicular to the longitudinal axis, and having first and second edges with a thickness extending along a normal axis that is perpendicular to both the longitudinal axis and the transverse axis, the stacking system comprising:
    a lift assembly, the lift assembly being configured to support the cementitious boards in a stacked arrangement upon the support surface, the lift assembly including a support fixture and a hoist, the support fixture having a support surface configured to support the cementitious boards such that the first and second faces of the cementitious boards are generally parallel to the support surface, and the hoist being connected to the support fixture and adapted to move the support fixture over a range of travel along the normal axis;
    a conveyor, the conveyor configured to serially convey the cementitious boards to a position over the lift assembly for being placed upon the support surface;
    a punch, the punch having a distal portion with a distal end, the distal portion being cylindrical;
    an actuator assembly, the actuator assembly being configured to reciprocally move the punch along the transverse axis relative to the support fixture over a measurement stroke between a home position, in which the distal end of the punch is in offset relationship to the cementitious boards supported in the support fixture, and a measurement position, in which the distal end of the punch is in interfering relationship with one of the cementitious boards supported in the support fixture, such that the actuator assembly drives the distal end of the punch into one of the first and second edges of said cementitious board when the punch moves from the home position to the measurement position;

a force gauge, the force gauge supported by the actuator assembly and interposed between the punch and the actuator assembly, the force gauge configured to measure a resistance force exerted against the punch by said cementitious board in response to the distal end of the punch being inserted into the edge of said cementitious board, the force gauge configured to generate a force signal indicative of the resistance force;

a processor, the processor in communication with the force gauge to receive the force signal therefrom, the processor programmed with an edge hardness measurement program stored on a non-transitory computer readable medium, the edge hardness measurement program being configured to use the force signal to determine the edge hardness value for the cementitious board.

6. The stacking system according to claim 5, wherein the edge hardness measurement program is configured to determine the edge hardness value based upon a peak load of the resistance force measured by the force gauge as the punch moves from the home position to the measurement position.

7. The stacking system according to claim 5, further comprising:

a backstop member, the backstop member positioned to stop the cementitious board from being moved via the conveyor such that the cementitious board is stopped at the position over the support surface of the lift assembly.

8. The stacking system according to claim 7, wherein the actuator assembly is mounted to the backstop member.

9. The stacking system according to claim 5, further comprising:

a controller, the controller being in operable arrangement with the actuator assembly, the controller configured to selectively operate the actuator assembly to reciprocally move the punch along the transverse axis over the measurement stroke.

10. The stacking system according to claim 9, wherein the actuator assembly includes a first actuator and a second actuator, the second actuator supporting the punch, the first actuator being configured to move the punch along the normal axis relative to the cementitious board supported in the support fixture to adjust the position of the punch relative to the thickness of the cementitious board, and the second actuator being configured to move the punch along the transverse axis relative to the cementitious board supported in the support fixture to adjust the position of the punch relative to the width of the cementitious board, the second actuator being configured to reciprocally move the punch along the transverse axis over the measurement stroke, and the force gauge is supported by the second actuator and is interposed between the punch and the second actuator.

11. The stacking system according to claim 10, further comprising:

a board detection system, the board detection system being configured to detect the position of the cementitious board supported in the support fixture along the normal axis, and the board detection system being configured to generate a board position signal indicative of the position of the cementitious board along the normal axis;

wherein the controller is in communication with the board detection system to receive the board position signal therefrom, the controller being configured to selectively operate the first actuator of the actuator assembly based upon the board position signal to move the punch along the normal axis to position the punch along the normal axis within the thickness of the cementitious board.

12. The stacking system according to claim 11, wherein the first face of the cementitious boards includes a pair of tapered portions respectively adjacent the first and second edges such that each cementitious board is asymmetrical about the transverse axis, and the board detection system is configured to detect the orientation of the first and second edges of the cementitious board supported in the support fixture relative to the punch and to generate a board orientation signal indicative of the orientation of the first and second edges of the cementitious board with respect to the punch to indicate which of the first and second edges of said cementitious board the punch is inserted into when the punch moves from the home position to the measurement position.

13. The stacking system according to claim 12, wherein the board detection system is configured to detect a center position along the normal axis between a pair of booked cementitious boards supported by the support fixture, the booked cementitious boards being in contacting relationship with each other such that the first edge of one cementitious board is aligned with the second edge of the other cementitious board, and the position signal the board detection system is configured to generate is a booked pair position signal indicative of the center position along the normal axis of the pair of booked cementitious boards, and wherein the controller is in communication with the board detection system to receive the booked pair position signal therefrom, the controller being configured to serially:

operate the first actuator of the actuator assembly based upon the booked pair position signal to move the punch along the normal axis to position the punch in a first pair position along the normal axis within the thickness of one of the pair of booked cementitious boards, operate the second actuator of the actuator assembly to reciprocally move the punch along the transverse axis over the measurement stroke, operate the first actuator of the actuator assembly based upon the booked pair position signal to move the punch along the normal axis to position the punch in a second pair position along the normal axis within the thickness of the other of the pair of booked cementitious boards, and operate the second actuator of the actuator assembly to reciprocally move the punch along the transverse axis over the measurement stroke.

14. A method of determining an edge hardness value of a cementitious board, the cementitious board having a cementitious core formed from aqueous cementitious slurry, the cementitious board having first and second faces with a length extending along a longitudinal axis and a width extending along a transverse axis that is perpendicular to the longitudinal axis, and having first and second edges with a thickness extending along a normal axis that is perpendicular to both the longitudinal axis and the transverse axis, the method comprising:

conveying the cementitious board to a position over a support surface of a lift assembly such that the support surface supports the cementitious board with the first and second faces being generally parallel to the support surface;

positioning a punch along the normal axis relative to the cementitious board supported by the support surface such that the punch is positioned along the normal axis within the thickness of the cementitious board;

moving the punch along the transverse axis relative to the cementitious board supported by the support surface over a measurement stroke between a home position, in which a distal end of the punch is in offset relationship to the cementitious board, and a measurement position, in which the distal end of the punch is in interfering relationship with the cementitious board, such that the distal end of the punch is inserted into one of the first and second edges of said cementitious board when the punch is in the measurement position;

measuring a resistance force exerted by the cementitious board against the punch in response to the punch being inserted into one of the first and second edges of said cementitious board;

transmitting a force signal to a processor, the force signal indicative of the measured resistance force;

executing an edge hardness measurement program stored upon a non-transitory computer-readable medium using the processor to determine the edge hardness value for the cementitious board based upon the force signal.

15. The method according to claim 14, further comprising:

displaying the edge hardness value in a display device operably arranged with the processor via a graphical user interface.

16. The method according to claim 14, wherein the edge hardness measurement program determines the edge hardness value based upon a peak load of the measured resistance force as the punch moves from the home position to the measurement position.

17. The method according to claim 14, wherein the first face of the cementitious board includes a pair of tapered portions respectively adjacent the first and second edges such that each cementitious board is asymmetrical about the transverse axis, and the method further comprising:

detecting the orientation of the first and second edges of the cementitious board supported by the support surface relative to the punch;

transmitting a board orientation signal to the processor, the board orientation signal indicative of the orientation of the first and second edges of the cementitious board with respect to the punch to indicate into which one of the first and second edges the punch was inserted.

18. The method according to claim 14, further comprising:

lowering the support surface of the lift assembly relative to a conveyor along the normal axis;

conveying a pair of booked cementitious boards to the position over the support surface of the lift assembly such that the support surface supports the pair of booked cementitious boards in a stacked arrangement upon the support surface.

19. The method according to claim 18, further comprising:

detecting the position along the normal axis of one of the cementitious boards in the stacked arrangement upon the support surface;

transmitting a board position signal to a controller, the board position signal indicative of the position of said cementitious board along the normal axis;

using the controller to move the punch along the normal axis based upon the board position signal to position the punch along the normal axis within the thickness of said cementitious board.

20. The method according to claim 18, wherein the first face of each of the pair of booked cementitious boards includes a pair of tapered portions respectively adjacent the first and second edges such that each of the booked cementitious boards is asymmetrical about the transverse axis, the pair of booked cementitious boards being in contacting relationship with each other such that the first edge of one cementitious board is aligned with the second edge of the other cementitious board, and the method further comprising:

detecting a center position along the normal axis between the pair of booked cementitious boards supported by the support fixture;

transmitting a booked pair position signal to a controller, the booked pair position signal indicative of the center position along the normal axis of the pair of booked cementitious boards;

detecting the orientation of the first and second edges of the pair of booked cementitious boards supported by the support surface relative to the punch;

transmitting a board orientation signal to the processor, the board orientation signal indicative of the orientation of the first and second edges of the pair of booked cementitious boards with respect to the punch;

using the controller to move the punch along the normal axis based upon the booked pair position signal to position the punch in a first pair position along the normal axis within the thickness of a first one of the pair of booked cementitious boards having the first edge adjacent the punch;

reciprocally moving the punch along the transverse axis over the measurement stroke for a first edge hardness measurement of the first edge of the first one of the pair of booked cementitious boards;

measuring the resistance force exerted by the first one of the pair of booked cementitious boards against the punch in response to the punch being inserted into the first edge of the first one of the pair of booked cementitious boards;

transmitting the force signal relating to the first edge hardness measurement to the processor, the force signal indicative of the measured resistance force for the first edge hardness measurement;

using the controller to move the punch along the normal axis based upon the booked pair position signal to position the punch in a second pair position along the normal axis within the thickness of the other one of the pair of booked cementitious boards having the second edge adjacent the punch;

reciprocally moving the punch along the transverse axis over the measurement stroke for a second edge hardness measurement of the second edge of the other one of the pair of booked cementitious boards;

measuring the resistance force exerted by the other one of the pair of booked cementitious boards against the punch in response to the punch being inserted into the second edge of the other cementitious board;

transmitting the force signal relating to the second edge hardness measurement to the processor, the force signal indicative of the measured resistance force for the second edge hardness measurement.

\* \* \* \* \*